United States Patent [19]

Smith

[11] Patent Number: 4,752,293
[45] Date of Patent: Jun. 21, 1988

[54] BARRIER CUSHION FOR INCONTINENT PATIENTS AND URINE COLLECTION SYSTEM COMPRISING THE SAME

[76] Inventor: Albert H. Smith, 439 Hillcross Avenue, South Morden, Surrey SN4 4BZ, England

[21] Appl. No.: 865,037
[22] PCT Filed: Sep. 10, 1985
[86] PCT No.: PCT/GB85/00411
   § 371 Date: May 9, 1986
   § 102(e) Date: May 9, 1986
[87] PCT Pub. No.: WO86/01710
   PCT Pub. Date: Mar. 27, 1986

[30] Foreign Application Priority Data

Sep. 11, 1984 [GB] United Kingdom ............... 8422940

[51] Int. Cl.$^4$ ............................................. A61M 1/00
[52] U.S. Cl. ............................. 604/322; 604/356;
   5/463; 5/464; 5/431; 5/90; 4/455; 4/456
[58] Field of Search ............... 604/317, 319, 322, 356,
   604/326; 128/132 R, 132 D; 4/450, 454–456,
   465, 483; 5/463, 462, 90, 464, 465, 431, 435, 437

[56] References Cited

U.S. PATENT DOCUMENTS

| | | |
|---|---|---|
| 1,341,564 | 5/1920 | King . |
| 1,395,879 | 11/1921 | Wallace .................................. 5/90 |
| 1,916,039 | 6/1933 | Chalmers . |
| 1,967,598 | 7/1934 | Stanley .................................. 4/456 |
| 2,085,296 | 6/1937 | Carey .............................. 128/132 R |
| 2,750,600 | 6/1956 | MacDonald ......................... 4/455 |
| 3,083,380 | 4/1963 | Adler .................................. 5/464 |
| 3,251,069 | 5/1966 | Clark .............................. 604/326 |
| 4,173,046 | 11/1979 | Gallagher . |
| 4,248,216 | 2/1981 | Glintz ............................. 128/132 D |
| 4,368,733 | 1/1983 | Sanidas . |
| 4,437,195 | 3/1984 | Mangels ................................. 4/450 |
| 4,522,447 | 6/1985 | Snyder et al. ......................... 5/464 |
| 4,533,352 | 8/1985 | Van Beek et al. ................. 604/317 |
| 4,536,902 | 8/1985 | McGill ................................. 4/455 |

FOREIGN PATENT DOCUMENTS

| | | | |
|---|---|---|---|
| 479265 | 3/1916 | France . | |
| 458775 | 12/1936 | United Kingdom ............... 604/356 |
| 822377 | 10/1959 | United Kingdom ................... 4/456 |
| 1178823 | 1/1970 | United Kingdom ................... 5/464 |
| 2063663 | 6/1981 | United Kingdom ................... 5/463 |

Primary Examiner—C. Fred Rosenbaum
Assistant Examiner—Mario Costantino
Attorney, Agent, or Firm—Merchant, Gould, Smith, Edell, Welter & Schmidt

[57] ABSTRACT

A cushion construction for positioning below a patient suffering from incontinence which is hygenic to use and which does not require permanent modification of a mattress or seat on which it is to be used is formed as a resilient body, particularly a foam block, having an upper surface (1) substantially parallel to its lower surface when the cushion is unstressed with the upper surface (1) being interrupted by a fluid collection and channelling area (3) including an inclined drainage plane extending downwardly into the body of the cushion to a drain hole (2) in an interior region thereof communicating the lowermost region of the inclined drainage plane with the underside of the resilient block. At least those surfaces of the cushion which will be contacted by urine will be covered with fluid impermeable sheet material (4). The cushion has optional urine collection systems either for use with a conventional incontinence pad or comprising a drainage duct (37) to a fluid container (38).

15 Claims, 4 Drawing Sheets

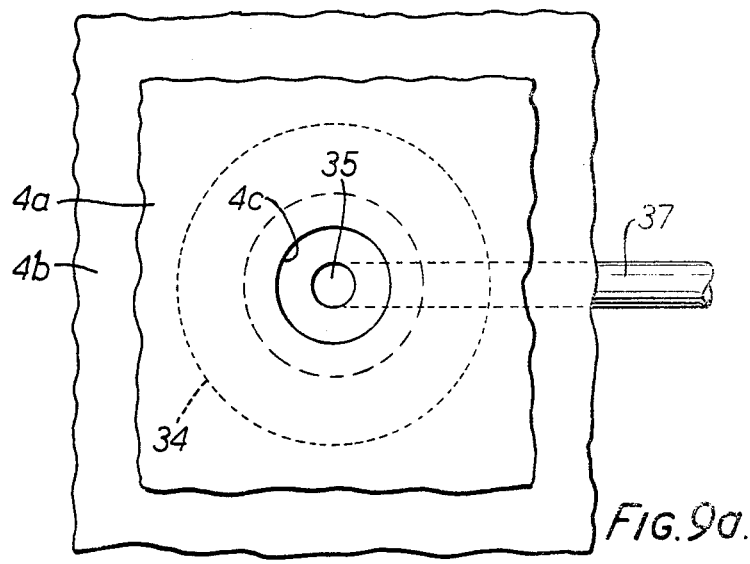
FIG.9a.
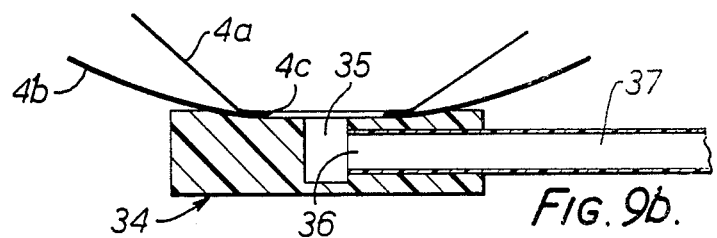
FIG.9b.
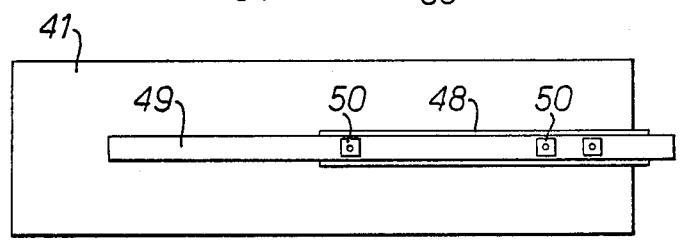
FIG.10a.
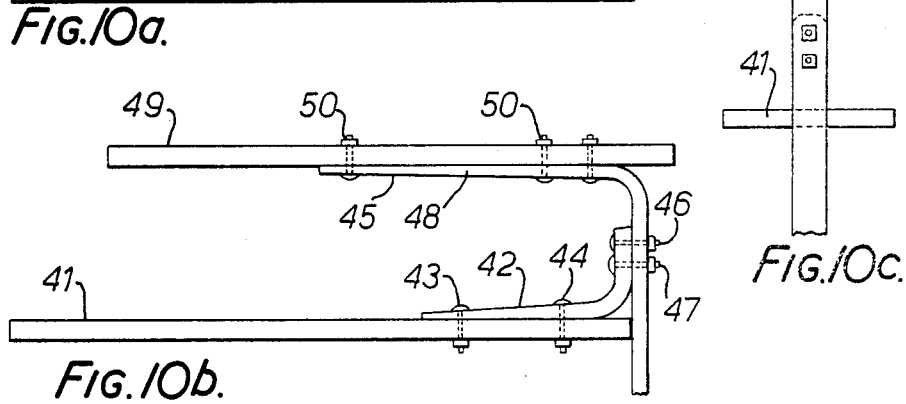
FIG.10b.
FIG.10c.

BARRIER CUSHION FOR INCONTINENT PATIENTS AND URINE COLLECTION SYSTEM COMPRISING THE SAME

This invention relates to the amelioration of the seating conditions to which a patient suffering from urine incontinence is subject and relates more particularly to a barrier cushion for this purpose and to urine removal systems comprising the same.

While it may not be possible to prevent urine incontinence, amelioration of the conditions to which a patient suffering from urine incontinence is subject is commonly achieved by seating a patient on an absorbant pad, frequently termed an incontinence pad, which is formed of wadding material on an impervious plastics film base and which is for taking up fluid passed by the patient. Such incontinence pads are however inefficient. They have only a limited capacity and become saturated, giving rise to a number of undesirable features. Apart from the basic discomfort to the patient of being in contact with cold urine, by virtue of the chemical content of urine, the wet or saturated pad inflames bed sores, retards their treatment, soils personal clothing and bedding and requires their frequent changing.

Alternatives to such simple incontinence pads which aim to remove from the immediate vicinity of the patient urine and/or faeces are proposed in a number of documents. These use a variety of approaches. Thus, for example, a conventional bed mattress has to be modified to receive a urine and/or faeces collecting device in U.S. Pat. Nos. 1,341,564, 1,395,879, 1,916,039, 4,096,596 and 4,368,733 and French Pat. No. 479,265, a drain system being proposed in each of these documents with the exception of U.S. Pat. No. 1,395,879. The principle of U.S. Pat. No. 4,096,596 is also applied to a chair. Such systems are relatively expensive to provide in requiring replacement of a conventional mattress on a bed by such specially modified mattresses and generally only provide the required urine/faeces removal facility at a single location which may not always be suited to the size of patient and his positioning in a bed.

An improved underpad for a patient which can be laid on a conventional mattress or seat is described in U.S. Pat. No. 4,173,046 which, while purporting to maintain a relatively dry top surface through its ability to store substantial volumes of liquid in an absorbent layer below a top cushioning layer, is still a disposable item which cannot be reused and is considerably more expensive to produce than the simple conventional incontinence pad.

It is an object of this invention to provide a reusable barrier cushion for use in instances of incontinence with either male or female patients which does not result in the patient sitting or lying in contact with urine and which does not require permanent modification of a mattress or seat.

According to the present invention, there is provided a barrier cushion construction for positioning below a patient suffering from incontinence and which is to communicate with storage means below a patient, which cushion is formed as a resilient body having an upper surface plane substantially parallel to its lower surface planes when unstressed, the upper surface plane being interrupted by an inclined drainage plane extending downwardly from a forward marginal region of the resilient body to a drain hole in an interior region thereof communicating the lowermost region of the inclined drainage plane with the lower surface plane of the resilient body, at least the inclined drainage plane and interior wall of the drain hole having urine-impermeable sheet material at its surface. Preferably, a urine-impermeable sheet material is located over the entire surface area of the resilient body including the interior wall of the drain hole which, thus lined, remains open for throughflow of urine for removal, for example as described hereinafter. The resilient body may be a plastics foam block having a continuous surface skin providing such sheet material. However it is preferred that such sheet material be a plastics film which envelopes the resilient body. Although it is preferred to form the resilient body as a foam block, it may be a cushion which is filled with a fluid medium, generally air or water, so that it assumes an appropriate shape, for which purpose the panels making up the cushion are appropriately shaped and joined.

The cushion of the present invention enables a patient to be protected from contact with urine. A patient made more comfortable in this manner will respond favourably to the treatment of bed sores. The cushion is suited for use with means for the removal of urine from its lower surface plane, as will be described hereinafter, the soiling of personal clothing and bedding will be avoided and there will be less frequent need for attention to be given to the patient.

Although the cushion may be formed as a single element, it is desirable to provide different degrees of resilience at different locations. This would mean different fluid pressures in different cushion regions of a divided cushion structure or the use of two or more types of foam. For convenience, the invention will be described hereinafter with reference to the use of two types of foam, although it should be understood that the principle of the invention is equally applicable to fluid filled cushions.

In one form of a foam cushion embodying this invention, the cushion is formed from a relatively thin lower layer of a firm foam bonded to a relatively thick upper layer of soft foam on which a patient is seated. In another cushion construction embodying this invention a firm foam is shaped to provide the flanks of the cushion to support the thighs of the patient which will be positioned thereon as well as provide a relatively thin lower foam layer of the cushion. A softer foam will again be used in the regions of the cushion on which a patient's buttocks are positioned. The soft foam which is employed in this way in the cushion of this invention may be a rubber latex product such as that sold under the trademark "Dunlopillo". The harder foam may be a chip foam product. It is indeed desirable for a harder foam to underlie at least that portion of the soft foam which provides normal seating comfort and which is not itself subject to body contact and in a preferred form of cushion embodying this invention, the cushion is formed from a plurality of foam elements fitting together in the manner of a three dimensional jigsaw to provide overall a body of foam shaped as a cushion embodying this invention.

Thus a preferred form of cushion embodying this invention comprises a first foam element of approximately T-shape and formed of a first and relatively soft foam material, the head of the T having the thickness of the cushion and the upright limb of the T, while defining part of the upper surface plane of the cushion, being of reduced thickness and not extending to the lower surface plane of the cushion; and a second foam element formed of a second and relatively hard foam material of substantially rectilinear configuration, having a maximum thickness equal to that of the first foam element and formed with a first cut-out matched to the dimensions of the said upright limb and a second cut-out from the upper surface plane of the cushion and having a base inclined towards the base of the first cut-out and terminating level with or below the base of the first cut-out, the foot of the upright limb of the first foam element and the foam of the second foam element located below said foot being recessed to form a vertical wall through the cushion which together with an opposed wall vertically delineating the end of said second cut-out provides a drain hole from the inclined base of the second cut-out.

The drain hole will generally be centrally positioned within the second foam element. To maximise the comfort to the patient, it is preferred that the aforesaid second foam element be in two parts, itself, the first part being of the harder foam material and having a band of foam extending thereacross at the end thereof opposite to that adjacent the head of the upright limb of the first foam element which is cut away from the upper surface plane to yield a flange thin in relation to lateral parts of the second foam element. The upper surface of the flange communicates with the drain hole over a surface optionally provided by a cut-out of greater depth than provided by the cutting away to form the said band, and the flange is surmounted by a third foam element which is formed of a soft foam, preferably the same foam as that of the first foam element, and comprises a cut-out narrowing towards the position of the drain hole and having a base inclined towards the drain hole, which inclined base communicates with the drain hole over an exposed portion of the surface of the flange of the second foam element.

The several foam elements thus assembled in the manner of a three-dimensional jig-saw are bonded together by means of a suitable adhesive. The completed cushion construction is then covered with plastics film. It is preferred for this purpose to employ two sheets of plastics film laid one on top of the cushion and one below and joined at the outer periphery of the cushion and at the position of the drain hole. The joining at the drain hole may be achieved by forming a cover sheet with a hole located at the drain hole and sealingly bonded around the hole perimeter and at its outer perimeter to the other plastics film sheet which is formed with a correspondingly positioned hole. The cover sheets are also joined at the perimeter of the cushion in like manner when a plug is placed in the bottom of the drain hole as will be described hereinafter and the film sheets are joined at the plug. With both systems, one plastics film is drawn through the drain hole to line it and the upper surfaces of the cushion while the other plastics film is passed over the lower surface plane of the cushion. Where the plastics films are brought together at the margins of the cushion, they may be adhesively taped together, welded or adhesively bonded together with appropriate trimming of the plastics film. An air valve to allow release of air will be provided in the plastics film.

The barrier cushion of the invention may, in one operative procedure, be employed over a conventional type of incontinence pad which will become a reservoir for storing urine which passes into it from the cushion of this invention and is discarded when saturated. Alternatively, it is preferred that the drain hole of the cushion communicate with a fluid receiver through an appropriate conduit. The latter procedure has the advantage that a fluid receiver can be employed which will hold a greater volume of fluid than an incontinence pad which, although out of contact with the patient, could still become saturated, suffer from outflow of excess urine and be unpleasant unless replaced. Moreover it is less costly since there is no need to have a supply of disposable incontinence pads available at all times.

For a better understanding of the invention and to show how the same can be carried into effect, reference will now be made by way of example to the accompanying drawings wherein:

FIG. 5b is a longitudinal section through the cap vortex element of FIG. 5a;

FIG. 6b is a longitudinal section through the pipe vortex element of FIG. 6a;

FIGS. 9a and 9b are respectively plan and sectional views through a cushion embodying this invention illustrating how the covering of the cushion with plastics film is achieved when the cushion is used as shown in FIG. 8;

FIG. 10a is a compression clip to be fitted on a mattress on which a cushion of the invention is to be employed according to FIG. 8;

FIG. 10b shows the compression clip in side elevation; and

FIG. 10c shows the compression clip in end elevation.

Figure 1:
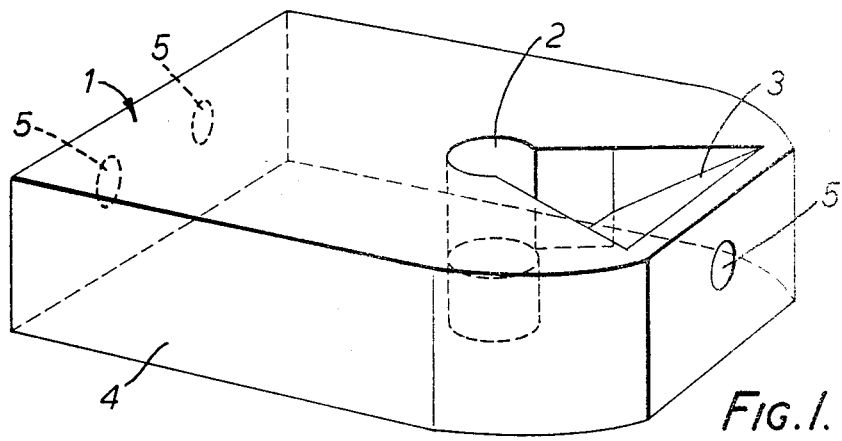
FIG. 1 is a perspective view from above and one side of an incontinence cushion embodying this invention.

Referring to FIG. 1, a fundamental construction of a barrier cushion embodying this invention for an incontinent patient for use with a barrier cushion or, when subject to slight change, with a siphoning system leading to a fluid receiver, has an upper surface 1 providing a seating area for a patient, a drain hole 2 and a fluid collection and channelling area 3 comprising an inclined plane to the drain hole 2. The cushion is covered with a surface sealing plastics cover 4 whose construction will be described in detail hereinafter. The cover has vents 5 at a number of locations therein. These vents may be merely eyelet apertures which can be closed with plugs (not shown) when washing the cushion after use. It is the provision and disposition of features 2 and 3 in the cushion 1 that are of fundamental importance to the invention in preventing any siting of urine on the upper surface 1 to be in contact with the patient both during the period of passing and as a result of "backflow" when it is rapidly draining away below the patient from the fluid collection and channelling area 3 and drain hole 2.

Figure 2:
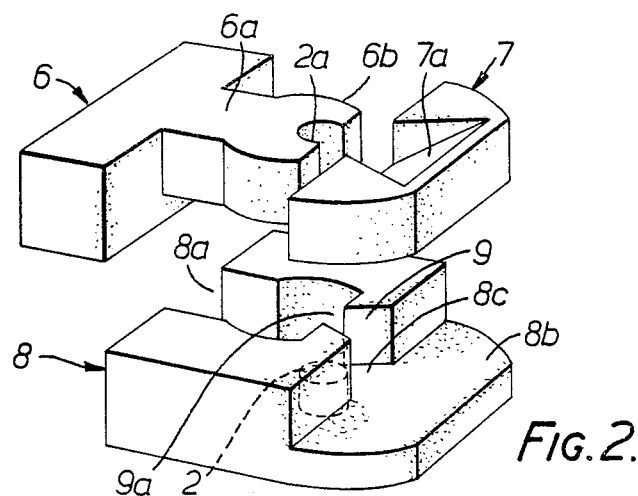
FIG. 2 is an exploded view of the three foam elements making up the cushion of FIG. 1.

The cushion itself can be formed as a single element from a single block of foam. However, it is preferably formed from a combination of foam materials of different hardness as illustrated, according to one preferred example, in FIG. 2 of the drawings which is an exploded view showing there to be three component elements. Thus, there is a T-shaped element 6, an end band element 7 and a lower element 8 which fit together in the manner of a solid jigsaw to form the monolithic structure suggested by FIG. 1. As will be apparent from FIG. 2, the individual elements contain regions of differing thickness which allow this fitting together. T-shaped element 6 has an upright limb 6a of the T of reduced thickness lying over a cut-out portion 8a of element 8. End band element 7 fits over a thin portion 8b of the lower element 8. An even thinner portion 8c lies between portions 8a and 8b of lower element 8, forming the floor of a guide duct 9 to the drain hole 2, above which there is a vertical or a conical incomplete wall portion 2a provided by the lower end of limb 6a of element 6 which is widened into a substantially circular portion 6b. A gap 9a in a recess wall 8a of element 8 is in line with wall portion 2a of element 6 so that the guide duct 9 can communicate with the drain hole 2. The end-band element 7 lying on the thin portion 8b provides an inclined surface 7a towards the portion 8c of element 8 for passage of urine towards the drain hole 2. The cushion can be constructed from a wide variety of materials including rubber, polyurethane, polyether etc. When the cushion is formed of the plurality of elements shown in FIG. 2, elements 6 and 7 are preferably formed of a relatively soft foam, such as rubber latex, and element 8 is preferably formed of a relatively hard foam such as a foam chip composite.

The precise dimensions of the barrier cushion, as well as its shape and contours, whereby it can be flexed longitudinally or transversely, the shape of the discharge hole and the guide duct thereto can be varied to suit the patient and functional nature of the cushion, for example whether it is to be used for a child or adult and whether to be used on a mattress, bed, chair, car seat, wheel chair etc. The proportions of the cushion shown in FIG. 1 represent a preferred cushion formation for use on top of a mattress. With such a construction, the combined capacity of the fluid collection and channel area 3 and the drainage site 2 will be at least 600 ml. The thickness of the cushion overall may then be from 4 to 6 cm, preferably 5 cm, the upright limb 6a and the end band element 7 having a thickness of from 3 to 4 cm, preferably 3.5 to 3.9 cm, more preferably 3.8 cm, the cut out portion 8a and flange 8b having a thickness of from 1 to 2 cm, preferably 1.5 to 1.9 cm, more preferably 1.2 cm and the portion 8c having a thickness of 0.4 to 0.8 cm, preferably 0.6 cm. The cushion will have length and width dimensions of 60 to 70 cm and 40 to 60 cm respectively, with the drain hole being positioned about 25 cm from the forward edge of the cushion.

Figure 3:
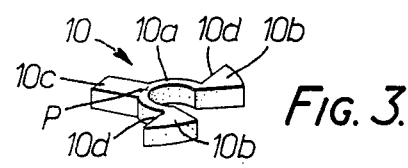
FIG. 3 is a perspective view of a ribbing element for emplacement around the drain hole of the cushion.
Figure 4:
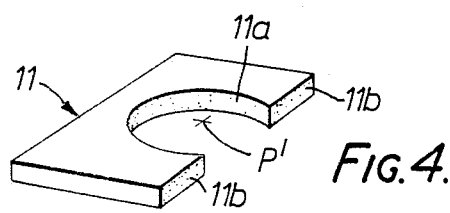
FIG. 4 is a perspective view of further ribbing material to be used in conjunction with that of FIG. 3.
Figure 5A:
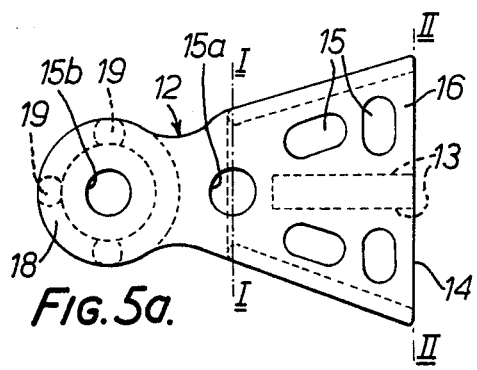
FIG. 5a shows in plan a cap vortex element for feeding fluid into the drain hole of the cushion of FIG. 1.
Figure 5C:
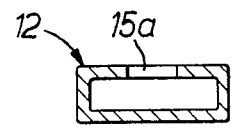
FIG. 5c is a transverse cross-section through the cap vortex element of FIG. 5a at I—I.
Figure 5B:
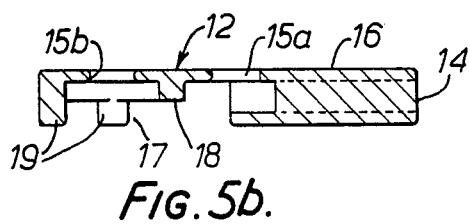
Figure 5D:
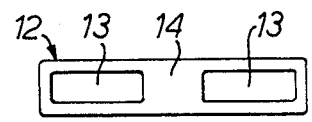
FIG. 5d is an end view of the cap vortex element of FIG. 5a, taken at II—II.
Figure 6A:
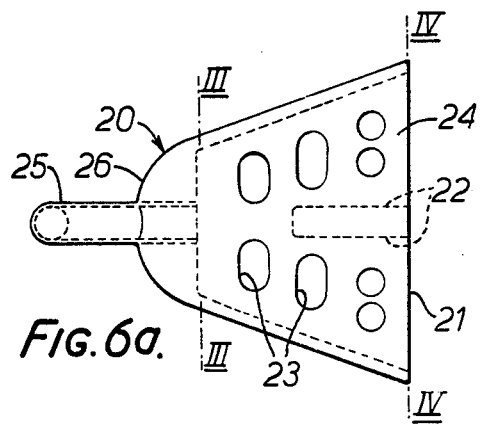
FIG. 6a is a plan view of a pipe vortex element for supply of urine to the drain hole of the cushion of FIG. 1.
Figure 6C:
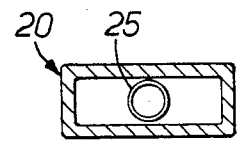
FIG. 6c is a transverse section at III—III through the pipe vortex element of FIG. 6a and FIG. 6d is an end view of the pipe vortex element of FIG. 6a taken at IV—IV.
Figure 6B:
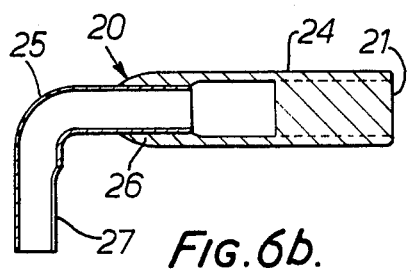
Figure 6D:
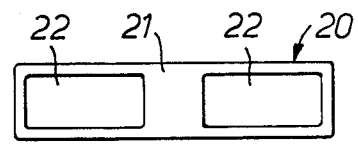

Additional comfort for a patient can be provided by fitting thin "ribbing" of soft foam material in a thickness of say 1.2 to 1.8 cm, preferably 1.5 cm with the above-dimensioned cushion on the upper surface of the cushion. Two such ribbing elements 10 and 11 are shown in FIGS. 3 and 4 respectively. Ribbing element 10 is of radial symmetry comprising an arcuate portion 10a for siting around the top edge of wall portion 2a of element 6 and having the same radius, two circular sectors 10b of larger maximum radius than portion 10a flanking the latter and a strip portion 10c for extending into the interior of circular portion 6b of element 6 extending radially back from arcuate portion 10a. Ribbing element 11 is of rectangular formation having a circular portion 11a cut out of it and is to be seated on elements 6 and 8 behind ribbing element 10 so that straight edges 11b on ribbing element 11 abut edges 10d on ribbing element 10. The centre point P of arcuate portion 10a then lies over the centre point P' of cut-out circular portion 11a.

The plastics cover sheet 4 of the cushion shown in FIG. 1 is formed from two cut plastics film pieces which are joined by fusion around the common circumference of a hole cut approximately central in each film area or sheet. In forming the plastics cover sheet 4, the aforesaid hole joining the films is placed concentric with the drain hole 2 at the lower plane of the cushion. The top film is pulled through the drain hole 2 and spread out over the upper surfaces of the cushion, including inclined surface 7a of the cushion. The bottom film is spread over the bottom surface of the cushion and wrapped around the bottom edge to meet the top film which is wrapped around the top edge of the cushion and the two films are united. This may be done with adhesive cloth tape, by the use of adhesive or by heat or solvent welding. The films can be chosen from a wide range of materials that satisfy the requirement of being impervious and hydrophobic to aqueous fluids e.g. rubber, polypropylene, polyvinyl chloride, polyethylene etc. The films forming cover 4 in FIG. 1 are polyethylene, 0.05 mm thick for the upper film and 0.13 mm thick for the bottom film although in other constructions the thickness of the films can be varied and the upper film may be of equal or different thickness from the lower film.

To provide a close fit of the cover 4 over the cushion shown in FIG. 1, pleats or folds which necessarily radiate from the drain hole over the seating surface 1 and inclined surface 3 are adhesively bonded, heat fused or solvent welded to each other.

It is a general requirement of the cushion of this invention that there should be a continuous and rapid flow of urine from the fluid collection and channelling area 3 into the drainage site under a wide variety of conditions determined for example by the size, weight and seating of the patient. To ensure that such rapid flow of urine down through drain hole 2 occurs under such a variety of conditions, in preferred practice a vortex channel is placed over the portion 8c of element 8 to communicate inclined surface 7a with drain hole 2.

Thus referring to FIGS. 5a to 5d of the drawings, there is shown in various views a vortex channel hereinafter referred to as a "cap vortex 12". The dimensions of the cap vortex 12 can be varied, but suitably the cap vortex has a length of 8 cm, a maximum width of 6 cm and a depth of 1.2 cm and the form of cap vortex of such dimensions and as shown in FIGS. 5a to 5d is suitable for use with a cushion of the type shown in FIG. 1. The vortex is preferably a moulded plastics body formed for example of rubber polyvinyl chloride, polypropylene or polyethylene as a semi-rigid shell having inlets 13 at its wide end 14 and apertures 15, 15a, 15b on its upper side 16 to provide access for the flow of fluid into the hollow shell where it is channelled via an exit port 17 into the drain hole 2. A further feature of the vortex cap is that the hollow shell structure extends on the apertured upper side 16 to form a circular disc 18 carrying one or more lugs 19 that can rest on or detachably press-fit into the preformed holes around the drain hole or in fluid distributor to be described hereinafter with reference to FIG. 7. Such a press-fit ensures better location of the vortex, while enabling it to be removed readily for washing. In a similar manner the "cap vortex 12" can rest on or detachably press-fit into preformed holes around the plug element 34 described hereinafter with reference to FIGS. 9a and 9b.

FIGS. 6a to 6d show an alternative design of vortex device hereinafter termed "a pipe vortex 20". This vortex again comprises a hollow shell of moulded plastics or rubber material open at its wide end 21 at inlets 22 and having apertures 23 on the upper side 24 thereof to provide access for flow of fluid into the hollow shell where it is channelled into a conduit 25 fitted at the closed end 26 of the vortex and which leads through a right angle bend into the drain hole 2 of a cushion embodying this invention with which the vortex is used. The pipe makes a press-fit with and is detachable from the preferably used fluid distributor to be described hereinafter with respect to FIG. 7 and includes an outlet aperture 27 to allow urine to leave laterally to disperse freely in the directional arms of the distributor. The dimensions of "pipe vortex 20" can be varied but the hollow body of the pipe vortex will, when used with the cushion of FIG. 1 preferably have a length of about 6 cm, a maximum width of about 7 cm and a depth of about 1.2 cm. The conduit 25 may conveniently have an outside diameter of from 7 to 9 mm and internal diameter of from 4 to 6 mm, preferably 6 mm. The wall thickness is generally not less than 1.5 mm.

Figure 7A:
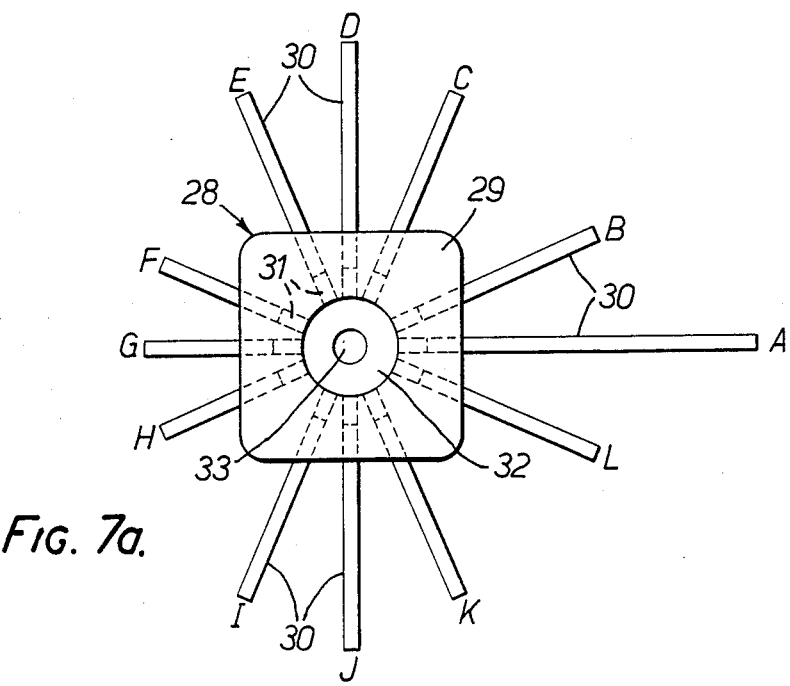
FIG. 7a is a plan view of a fluid distributor for use between a cushion embodying this invention and a conventional incontinence pad.
Figure 7B:
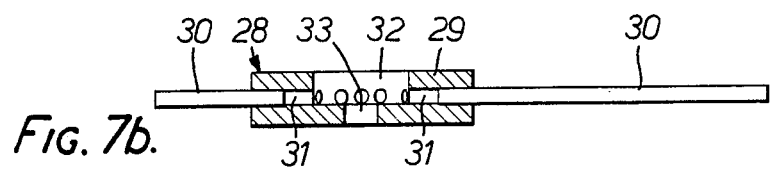
FIG. 7b is a transverse cross-section through the fluid distributor of FIG. 7a; taken at V—V.

Referring next to FIGS. 7a and 7b of the drawings, there is shown a fluid distributor 28 which assists in the rapid and uniform dispersion of the urine which passes through the drain hole 2 of the barrier cushion shown in FIG. 1, out of a circular hole in the cover 4 located at the base of the drain hole into an absorption or incontinence pad (not shown) placed under the cushion of FIG. 1 to receive urine. The fluid distributor 28 serves to ensure that there is no build up of fluid around the bottom of the drain hole 2 with consequent backflow of fluid into the guide duct 9 (see FIG. 2) of the cushion and beyond with consequent discomfort to the patient. The dimensions of the distributor 28 will be matched to the dimensions of the barrier cushion and the incontinence pad to be placed below it and the fluid distributor is preferably made from a plastics material such as rubber or polyethylene. The fluid distributor consists of a hollow plastics base 29 whose lateral walls are drilled to receive a number of plastics dispersing tubes 30 disposed around its perimeter. Channels 31 receiving the dispersing tubes are drilled radially towards a central area 32 which is located, in use, below the drain hole 2 of the cushion shown in FIG. 1. The central area 32 provides a hole 33 to receive the pipe fitting 25 of the pipe vortex 20 shown in FIGS. 6a to 6d, if used, and, from the outlet aperture 27 of which pipe fitting 25 urine will pass in use, into the central area 32 and then out through tubes 30. In addition small holes (not shown) on the upper surface of the base 29 receive the lugs 19 of the disc 18 on the vortex 12 of FIGS. 5a to 5d, if used.

To ensure that fluid is distributed as rapidly as possible over the maximum extent of the incontinence pad, the tubes 30 are of differing lengths, thereby extending to different distances from the centre of the base 29. The individual tubes bear letters A to L and the following table shows the extent to which these may project beyond the square base 29. Each tube may conveniently have an internal diameter of about 4 mm and an external diameter of about 7 mm and wall thickness of 1.5 mm.

TABLE

| Tube | Projection cm |
| --- | --- |
| A | 13.5 |
| B | 9.5 |
| C | 9.5 |
| D | 10.0 |
| E | 9.5 |
| F | 3.0 |
| G | 3.0 |
| H | 3.0 |
| I | 9.5 |
| J | 10.0 |
| K | 9.5 |
| L | 9.5 |

As an alternative to using an incontinence pad and associated fluid distributor according to FIGS. 7a and 7b, urine may be removed from the immediate vicinity of the barrier cushion to an external storage device such as a bottle or sac whose size can be selected with a wide range of dimensions so as to be in excess of the capacity of an incontinence pad. Thus, referring to FIG. 8 of the accompanying drawings in which like reference numerals denote like parts in FIG. 1, a barrier cushion preferably having the construction shown in FIG. 2 and preferably employed with the vortex element of either FIGS. 5a to 5d or of FIGS. 6a to 6d is additionally provided with a plug element 34 (see FIGS. 9a and 9b) situated at the bottom of drain hole 2 to close it off and which is joined to the cover 4 as a permanent feature so that the bottle or sac, associated conduit and the plug can be regarded as appendages of the cushion. However for simplicity of description they will not be discussed hereinafter in such terms. The plug element is formed as a moulded plastics body drilled with inlet passage 35 and outlet passage 36 (see FIG. 9b). Extending from outlet passage 36 is a plastics conduit 37 which has an internal diameter of 6 mm, external diameter of 9 mm and wall thickness of 1.5 mm and which passes under the cushion to a plastics fluid receiver 38 in which urine can be collected in greater amount than in an incontinence pad. The conduit 37 may be fitted internally with a thin metal helix, e.g. of anodised aluminium, to assist the flow of urine along the essentially hydrophobic walls of the conduit. The fluid receiver 38 possesses an opening 39 in its top which, when open (a closure 40 is provided), prevents any back pressure developing and opposing syphon action as liquid rises in the fluid receiver.

FIGS. 9a and 9b not only show the plug element but plastics cover films 4a and 4b which in contrast to the equivalent cover films used for forming the cover 4 of a cushion as shown in FIG. 1 to be used with an incontinence pad, are adhesively bonded or heat fused or solvent welded, not only to each other, but also to the plug element 34 over which they are fitted with apertures 4c in each in alignment with each other and concentric with inlet passage 35 into the plug element, FIGS. 9a and 9b show the plug element/plastics film combinations as they will be before use in wrapping the foam interior of the cushion. Once the plug element has been placed underneath the drain hole the plastics cover films will be handled in like manner to the plastics films described hereinbefore in connection with the enveloping of the foam interior of the cushion of FIG. 1. The aforementioned remarks concerning film material and thickness are equally applicable here.

Figure 8:
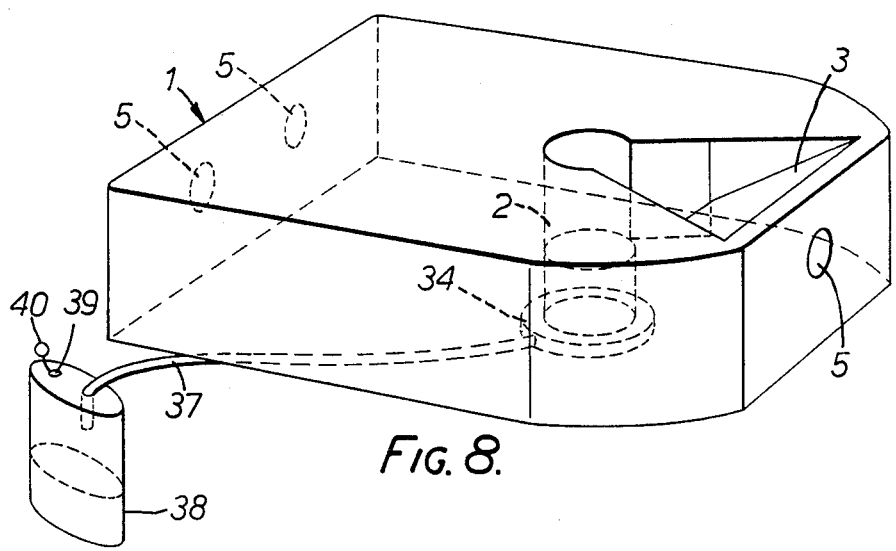
FIG. 8 is a perspective view from above of the cushion of FIG. 1 in association with a fluid receiver.

When the fluid conduit system of FIGS. 8 to 9b is used by a patient in bed, flow from the drain hole 2 into the fluid receiver 38 may be prevented if a patient possesses sufficient weight to depress the mattress of the bed and cause the conduit 37 to assume an upwardly inclined path rather than an overall downward path for gravity feed to the fluid receiver 38. In order to ensure that syphonic action is maintained for fluid flow to the fluid receiver to occur, use is made of a compression clip arrangement as shown in FIGS. 10a to 10c of the accompanying drawings. The aim of this is to compress a narrow channel in the mattress to the side of the patient adjacent a barrier cushion according to this invention on which he or she is lying so that its upper surface between the cushion and the edge of the bed does not rise to a level above that at which urine leaves the drain hole of the cushion to enter fluid conduit 37. A simple form of clamping arrangement comprises plywood support strip 41 placed below the mattress and having the lower reinforcing mild steel bracket 42 of a pair of such brackets bolted to it at 43,44. The upper steel bracket 45 is bolted to the lower bracket 42 by a pair of bolts 46,47 with the overlap between the brackets being determined by the compression required on the mattress on which the arrangement is to be used. The brackets between them define a U-shaped element reducing the natural thickness of the mattress into a compressed channel to carry the conduit 37 so that, under body weight of a patient, spontaneous flow proceeds by gravity and siphon action. If desired a single doubly bent metal strip member may replace the pair of brackets. Bolted to the upper limb 48 of the U-shaped element is an inverted channel member 49 of metal. The bolting is through bolts 50. With the compression clip shown in FIGS. 10a to 10c the fluid conduit passes under the channel member 49 as far as the first bolt 50 and then under the upper steel bracket 45 toward the edge of the mattress where it is directed downwardly to the fluid receiver 38 shown in FIG. 8. Hence the required through passage of urine through the fluid conduit will be maintained.

Alternatively the channel member 49 can be wider than that shown in FIGS. 10a to 10c so that bolts 50 can be so located as to allow the fluid conduit to travel uninterruptedly through the length of the channel member 49 and be directed downwardly to the fluid receiver from the point at which it leaves the channel member 49.

I claim:

1. A barrier cushion for positioning below a patient suffering from incontinence and which is to communicate with urine storage means below a patient, the cushion comprising a resilient body having an upper surface and a lower surface substantially parallel thereto when the cushion is in an unstressed condition, the upper surface being interrupted by a fluid collection and channelling area including an inclined trapezoidal drainage plane extending into and through the resilient body from a forward marginal region thereof to a drain hole in an interior region of the resilient body, the drain hole communicating the lowermost region of the inclined drainage plane with the lower surface of the resilient body, urine-impermeable sheet material at the surfaces at least of the inclined drainage plane and the interior wall of the drain hole, and a drain hole protecting duct-member disposed at a lowermost region of the inclined drainage plane, which duct-member is a rigid hollow body having a trapezoidal portion including a narrow end surface adjacent the drain hole and a wider end surface extending over and at least partially covering the inclined drainage plane, the hollow body being formed with openings in its upper surface and openings at its wider end surface for receiving urine, and outlet means at its narrow end constructed and arranged to direct a downward flow of urine into the drain hole.

2. A barrier cushion as claimed in claim 1, wherein the resilient body comprises a plastics foam block.

3. A barrier cushion as claimed in claim 1 wherein the resilient body possesses a resilience which is non-uniform over the entire upper surface thereof.

4. A barrier cushion as claimed in claim 3 which comprises seating and thigh-supporting zones of different resilience, the cushion having a seating zone comprising a lower firm foam layer and an upper softer foam layer and having a thigh-supporting firm foam zone.

5. A barrier cushion as claimed in claim 4 wherein the soft foam is a rubber latex foam and the firm foam is a chip foam material.

6. A barrier cushion, as claimed in claim 4 which comprises a first foam element comprising a relatively soft first foam material and having a limb portion with a transverse head portion situated across one end thereof and a foot region at the other end thereof; said first foam elements comprising a T-shaped member, the transverse head portion having a thickness substantially equal to a thickness of the cushion; and, a remainder of the first foam element defining part of the upper surface of the cushion and having a reduced thickness relative to the transverse head portion and not extending to the lower surface of the cushion; and, a second foam element formed of a second and relatively hard foam material, the second foam element having a substantially rectilinear configuration and a maximum thickness substantially equal to a maximum thickness of the first foam element and having a first cut-out portion matched to dimensions of the said limb portion and having a base parallel to the lower surface of the cushion at a depth substantially equal in magnitude to the thickness of said limb portion, and a second cut-out extending substantially through the entire thickness of the second foam element from the upper surface of the cushion defining said inclined drainage plane descending into and through the second foam element, the foot region of said limb portion of the first foam element and a region of the second foam element located below said foot region being recessed to form a wall through the cushion together with an opposed wall vertically delineating an end surface of said second cut-out, provides said drain hole.

7. A barrier cushion as claimed in claim 6 wherein the second foam element comprises two parts consisting of a first part formed of said relatively hard foam material having a first portion whose thickness is equal to the thickness of the cushion and which has a longitudinally extending channel providing a part of said second cut-out receiving said limb portion and having a base formed with an opening therethrough constituting said drain hole, said first part having a second portion whose base surface is continuous with the base surface of the first portion, an upper surface leading to said drain hole and a thickness which is less than that of the remainder of said first part, which second portion extends across the width of said cushion; and a second part formed of a soft foam material which overlies said second portion of the first part of the second foam element to leave exposed an upper surface region thereof; said second part including said cut-out narrowing towards the position of the drain hole and having a surface inclined towards and in communication with the drain hole, which inclined surface communicates with the drain hole over said exposed upper surface region of said second portion of the first part of the second foam element.

8. A barrier cushion as claimed in claim 7 wherein the base of said channel possesses a smaller thickness than the second portion of the first part of the second foam element and the said second portion comprises an inclined upper surface region which provides a continuation of the inclined surface of the cut-out in the second part of the second foam element.

9. A barrier cushion as claimed in claim 1 wherein the urine-impermeable sheet material is a plastics film completely enveloping the cushion, which plastics film comprises two elements sealingly connected at the periphery of the cushion and having holes therein in coincidence with the drain hole at which the elements are sealingly connected together to provide a lining for the drain hole.

10. A barrier cushion as claimed in claim 1 whose drain hole protecting duct member includes a plate portion positioned adjacent thereof as an extension of a duct member upper surface, which plate portion surmounts the drain hole for directing urine issuing from said narrow end downwardly into the drain hole.

11. A barrier cushion as claimed in claim 1 wherein a tubular member communicates the narrow end of the trapezoidal portion of the hollow body of the urine collecting member with the drain hole.

12. A barrier cushion as claimed in claim 1 in combination with: a distributor device positioned below the drain hole thereof; a replacable incontinence pad formed of wadding material on an impervious base disposed below the distributor device, to form a urine collecting and storage system for an incontinent patient, the distributor device consisting of a plate member formed with a central recess operatively positioned below the cushion drain hole and with a plurality of drainage passages radiating from the central recess with housing tubes extending therefrom; and, a tube communicating the outlet means of the duct member with the distributor device.

13. The combination of claim 12 wherein respective said tubes radiating from the central recess possess different lengths.

14. A barrier cushion as claimed in claim 1 in combination with: a plug member in said drain hole and having a passage therethrough; a storage container; a tube communicating the passage in the plug member with the storage container thereby to form a urine collecting and storage system for use with an incontinent patient; and, a tube communicating the outlet means of the duct member with the plug member.

15. The combination claimed in claim 14 which is in use in association with a bed mattress and additionally comprises clamp means for placing over the edge of a said mattress adjacent to said barrier cushion, the clamp means comprising a channel member located on the upper surface of the mattress and which is sized to receiving the duct means and maintain it substantially horizontal irrespective of the extent to which the mattress is depressed by a patient.

* * * * *